US009039610B2

(12) United States Patent
Wilkins et al.

(10) Patent No.: US 9,039,610 B2
(45) Date of Patent: May 26, 2015

(54) THORACIC ACCESS PORT

(75) Inventors: Rebecca Ann Wilkins, Royston (GB);
Cormac O'Prey, Bishops Stortford (GB); Valerie Anne Scott, Cambridge (GB)

(73) Assignee: Covidien LP, Mansfield, MA (US)

( * ) Notice: Subject to any disclaimer, the term of this patent is extended or adjusted under 35 U.S.C. 154(b) by 512 days.

(21) Appl. No.: 13/445,118

(22) Filed: Apr. 12, 2012

(65) Prior Publication Data

US 2012/0296170 A1 Nov. 22, 2012

Related U.S. Application Data

(60) Provisional application No. 61/487,867, filed on May 19, 2011.

(51) Int. Cl.
*A61B 1/32* (2006.01)
*A61B 17/34* (2006.01)
*A61B 17/02* (2006.01)
*A61B 17/00* (2006.01)

(52) U.S. Cl.
CPC ......... *A61B 17/3423* (2013.01); *A61B 17/0293* (2013.01); *A61B 2017/3427* (2013.01); *A61B 2017/347* (2013.01); *A61B 2017/00407* (2013.01); *A61B 2017/0237* (2013.01)

(58) Field of Classification Search
CPC ................. A61B 2017/00407; A61B 17/0293; A61B 17/3423; A61B 2017/3427
USPC ...................... 600/201–249; 403/83, 104–106
See application file for complete search history.

(56) References Cited

U.S. PATENT DOCUMENTS

| 1,780,912 | A | 11/1930 | Gau |
| 1,810,466 | A | 6/1931 | Deutsch |
| 2,313,164 | A | 3/1943 | Nelson |
| 2,541,516 | A | 2/1951 | Ivory et al. |

(Continued)

FOREIGN PATENT DOCUMENTS

| DE | 10001695 A1 | 2/2001 |
| DE | 102009014527 A1 | 9/2010 |

(Continued)

OTHER PUBLICATIONS

EP Search Report 11 25 0163 dated Jul. 6, 2011.

(Continued)

*Primary Examiner* — Matthew Lawson
*Assistant Examiner* — Si Ming Lee

(57) ABSTRACT

A surgical access assembly for positioning within an opening in tissue including an outer frame positionable outside a patient and defining an opening therein dimensioned to receive a surgical instrument therethrough. The outer frame includes first and second portions. The first portion is biased into locking engagement with the second portion such that a first engagement structure is in locking engagement with a second engagement structure. An inner member is positionable within a patient and a flexible member extends between the inner member and outer member and is operatively associated with the outer member. The first portion is movable to overcome the bias to move the first and second engagement structures to a disengaged position, wherein in the disengaged position at least one of the first and second portions is movable with respect to the other portion to adjust the tension on the flexible member to retract tissue.

10 Claims, 12 Drawing Sheets

(56) References Cited

U.S. PATENT DOCUMENTS

| | | | |
|---|---|---|---|
| 2,812,758 | A | 11/1957 | Blumenschein |
| 3,782,370 | A | 1/1974 | McDonald |
| 3,807,393 | A | 4/1974 | McDonald |
| 3,965,890 | A | 6/1976 | Gauthier |
| 4,130,113 | A | 12/1978 | Graham |
| 4,263,899 | A | 4/1981 | Burgin |
| 4,553,537 | A | 11/1985 | Rosenberg |
| 5,007,900 | A | 4/1991 | Picha et al. |
| 5,052,374 | A | 10/1991 | Alvarez-Jacinto |
| 5,080,088 | A | 1/1992 | LeVahn |
| 5,125,396 | A | 6/1992 | Ray |
| 5,169,387 | A | 12/1992 | Kronner |
| 5,231,974 | A * | 8/1993 | Giglio et al. ............... 600/206 |
| 5,232,451 | A | 8/1993 | Freitas et al. |
| 5,269,754 | A | 12/1993 | Rydell |
| 5,279,575 | A | 1/1994 | Sugarbaker |
| 5,330,501 | A | 7/1994 | Tovey et al. |
| 5,346,484 | A | 9/1994 | Van Lindert |
| 5,391,156 | A | 2/1995 | Hildwein et al. |
| 5,437,683 | A | 8/1995 | Neumann et al. |
| 5,445,615 | A | 8/1995 | Yoon |
| 5,460,170 | A | 10/1995 | Hammerslag |
| 5,480,410 | A | 1/1996 | Cuschieri et al. |
| 5,490,843 | A | 2/1996 | Hildwein et al. |
| 5,503,617 | A | 4/1996 | Jako |
| 5,520,610 | A | 5/1996 | Giglio et al. |
| 5,524,644 | A | 6/1996 | Crook |
| 5,556,385 | A | 9/1996 | Andersen |
| 5,562,677 | A | 10/1996 | Hildwein et al. |
| 5,653,705 | A | 8/1997 | de la Torre et al. |
| 5,697,891 | A | 12/1997 | Hori |
| 5,728,103 | A | 3/1998 | Picha et al. |
| 5,755,660 | A | 5/1998 | Tyagi |
| 5,755,661 | A | 5/1998 | Schwartzman |
| 5,772,583 | A | 6/1998 | Wright et al. |
| 5,776,110 | A | 7/1998 | Guy et al. |
| 5,779,629 | A | 7/1998 | Hohlen |
| 5,788,630 | A | 8/1998 | Furnish |
| 5,803,921 | A | 9/1998 | Bonadio |
| 5,810,721 | A | 9/1998 | Mueller et al. |
| 5,846,193 | A | 12/1998 | Wright |
| 5,875,782 | A | 3/1999 | Ferrari et al. |
| 5,879,291 | A | 3/1999 | Kolata et al. |
| 5,906,577 | A | 5/1999 | Beane et al. |
| 5,908,382 | A | 6/1999 | Koros et al. |
| 5,931,778 | A | 8/1999 | Furnish |
| 5,935,107 | A | 8/1999 | Taylor et al. |
| 5,944,736 | A | 8/1999 | Taylor et al. |
| 5,951,466 | A | 9/1999 | Segermark et al. |
| 5,951,467 | A | 9/1999 | Picha et al. |
| 5,957,835 | A | 9/1999 | Anderson et al. |
| 5,967,972 | A | 10/1999 | Santilli et al. |
| 5,993,385 | A | 11/1999 | Johnston et al. |
| 6,024,736 | A | 2/2000 | de la Torre et al. |
| 6,033,362 | A | 3/2000 | Cohn |
| 6,033,425 | A | 3/2000 | Looney et al. |
| 6,033,426 | A | 3/2000 | Kaji |
| 6,036,641 | A | 3/2000 | Taylor et al. |
| 6,048,309 | A | 4/2000 | Flom et al. |
| 6,074,380 | A | 6/2000 | Byrne et al. |
| 6,113,535 | A | 9/2000 | Fox et al. |
| 6,120,436 | A | 9/2000 | Anderson et al. |
| 6,132,370 | A | 10/2000 | Furnish et al. |
| 6,142,935 | A | 11/2000 | Flom et al. |
| 6,159,231 | A | 12/2000 | Looney et al. |
| 6,162,172 | A | 12/2000 | Cosgrove et al. |
| 6,231,506 | B1 | 5/2001 | Hu et al. |
| 6,254,533 | B1 | 7/2001 | Fadem et al. |
| 6,254,534 | B1 | 7/2001 | Butler et al. |
| 6,283,912 | B1 | 9/2001 | Hu et al. |
| 6,309,349 | B1 | 10/2001 | Bertolero et al. |
| 6,312,377 | B1 | 11/2001 | Segermark et al. |
| 6,331,158 | B1 | 12/2001 | Hu et al. |
| 6,332,468 | B1 | 12/2001 | Benetti |
| 6,354,995 | B1 | 3/2002 | Hoftman et al. |
| 6,361,492 | B1 | 3/2002 | Santilli |
| 6,382,211 | B1 | 5/2002 | Crook |
| 6,443,957 | B1 | 9/2002 | Addis |
| 6,450,983 | B1 | 9/2002 | Rambo |
| 6,458,079 | B1 | 10/2002 | Cohn et al. |
| 6,500,116 | B1 | 12/2002 | Knapp |
| 6,517,563 | B1 | 2/2003 | Paolitto et al. |
| 6,547,725 | B1 | 4/2003 | Paolitto et al. |
| 6,585,442 | B2 | 7/2003 | Brei et al. |
| 6,599,240 | B2 | 7/2003 | Puchovsky et al. |
| 6,599,292 | B1 | 7/2003 | Ray |
| 6,616,605 | B2 | 9/2003 | Wright et al. |
| 6,652,454 | B2 | 11/2003 | Hu et al. |
| 6,723,044 | B2 | 4/2004 | Pulford et al. |
| 6,730,021 | B2 | 5/2004 | Vassiliades, Jr. et al. |
| 6,730,022 | B2 | 5/2004 | Martin et al. |
| 6,746,396 | B1 | 6/2004 | Segermark et al. |
| 6,746,467 | B1 | 6/2004 | Taylor et al. |
| 6,814,078 | B2 | 11/2004 | Crook |
| 6,814,700 | B1 | 11/2004 | Mueller et al. |
| 6,840,951 | B2 | 1/2005 | de la Torre et al. |
| 6,846,287 | B2 | 1/2005 | Bonadio et al. |
| 6,958,037 | B2 | 10/2005 | Ewers et al. |
| 7,033,319 | B2 | 4/2006 | Pulford et al. |
| 7,052,454 | B2 * | 5/2006 | Taylor ............... 600/114 |
| 7,144,368 | B2 | 12/2006 | Larson et al. |
| 7,147,599 | B2 | 12/2006 | Phillips et al. |
| 7,179,225 | B2 | 2/2007 | Shluzas et al. |
| 7,195,592 | B2 | 3/2007 | Ravikumar et al. |
| 7,220,228 | B2 | 5/2007 | Hu et al. |
| 7,226,451 | B2 | 6/2007 | Shluzas et al. |
| 7,229,408 | B2 | 6/2007 | Douglas et al. |
| 7,238,154 | B2 | 7/2007 | Ewers et al. |
| 7,261,688 | B2 | 8/2007 | Smith et al. |
| 7,270,632 | B2 | 9/2007 | Santilli |
| 7,300,399 | B2 | 11/2007 | Bonadio et al. |
| 7,344,495 | B2 | 3/2008 | Ravikumar et al. |
| 7,387,126 | B2 | 6/2008 | Cox et al. |
| 7,393,322 | B2 | 7/2008 | Wenchell |
| 7,473,222 | B2 | 1/2009 | Dewey et al. |
| 7,507,202 | B2 | 3/2009 | Schoellhorn |
| 7,507,235 | B2 | 3/2009 | Keogh et al. |
| 7,537,564 | B2 | 5/2009 | Bonadio et al. |
| 7,540,839 | B2 | 6/2009 | Butler et al. |
| 7,559,893 | B2 | 7/2009 | Bonadio et al. |
| 7,566,302 | B2 | 7/2009 | Schwer |
| 7,585,277 | B2 | 9/2009 | Taylor et al. |
| 7,594,888 | B2 | 9/2009 | Raymond et al. |
| 7,650,887 | B2 | 1/2010 | Nguyen et al. |
| 2001/0002429 | A1 | 5/2001 | Hu et al. |
| 2001/0020121 | A1 | 9/2001 | Hu et al. |
| 2001/0041827 | A1 | 11/2001 | Spence et al. |
| 2002/0004628 | A1 | 1/2002 | Hu et al. |
| 2002/0095139 | A1 | 7/2002 | Keogh et al. |
| 2002/0099269 | A1 | 7/2002 | Martin et al. |
| 2002/0099271 | A1 | 7/2002 | Knapp |
| 2002/0137989 | A1 | 9/2002 | Clem et al. |
| 2003/0191371 | A1 | 10/2003 | Smith et al. |
| 2004/0049099 | A1 | 3/2004 | Ewers et al. |
| 2004/0054353 | A1 | 3/2004 | Taylor |
| 2004/0059192 | A1 | 3/2004 | Cartier et al. |
| 2004/0225195 | A1 | 11/2004 | Spence et al. |
| 2005/0096508 | A1 | 5/2005 | Valentini et al. |
| 2005/0171403 | A1 | 8/2005 | Paolitto et al. |
| 2005/0228232 | A1 | 10/2005 | Gillinov et al. |
| 2005/0267336 | A1 | 12/2005 | Bertolero et al. |
| 2005/0283050 | A1 | 12/2005 | Gundlapalli et al. |
| 2006/0004261 | A1 | 1/2006 | Douglas |
| 2006/0089537 | A1 | 4/2006 | Schoellhorn |
| 2006/0106416 | A1 | 5/2006 | Raymond et al. |
| 2006/0129165 | A1 | 6/2006 | Edoga et al. |
| 2006/0149137 | A1 | 7/2006 | Pingleton et al. |
| 2006/0149306 | A1 | 7/2006 | Hart et al. |
| 2006/0155170 | A1 | 7/2006 | Hanson et al. |
| 2007/0027364 | A1 | 2/2007 | Schwer |
| 2007/0073110 | A1 | 3/2007 | Larson et al. |
| 2008/0132766 | A1 | 6/2008 | Dant et al. |
| 2008/0234550 | A1 | 9/2008 | Hawkes et al. |
| 2009/0204067 | A1 | 8/2009 | Abu-Halawa |

(56) References Cited

U.S. PATENT DOCUMENTS

| | | |
|---|---|---|
| 2009/0265941 A1 | 10/2009 | Kurrus |
| 2009/0299148 A1 | 12/2009 | White et al. |
| 2010/0210916 A1 | 8/2010 | Hu et al. |
| 2010/0234689 A1 | 9/2010 | Wagner et al. |

FOREIGN PATENT DOCUMENTS

| | | | |
|---|---|---|---|
| EP | 0177177 | A2 | 4/1986 |
| EP | 2179699 | A1 | 4/2010 |
| EP | 2228014 | A1 | 9/2010 |
| EP | 2228024 | A1 | 9/2010 |
| EP | 2238931 | A1 | 10/2010 |
| EP | 2417922 | A1 | 2/2012 |
| GB | 2275420 | A | 8/1994 |
| WO | 95/00197 | A1 | 1/1995 |
| WO | 95/15715 | A1 | 6/1995 |
| WO | 01/08563 | A2 | 2/2001 |
| WO | 03/034908 | A2 | 5/2003 |
| WO | 2005/089655 | A1 | 9/2005 |
| WO | 2010/136805 | A1 | 12/2010 |
| WO | 2011/079374 | A1 | 7/2011 |

OTHER PUBLICATIONS

EP Search Report 11 25 0164 dated Aug. 6, 2011.
EP Search Report 11 25 0719 dated Nov. 16, 2011.
EP Search Report 11 18 9987 dated Feb. 15, 2012.
EP Search Report 12160423.5 dated Jun. 25, 2012.
European Search Report EP 12180474 dated Nov. 12, 2012.
Partial European Search Report EP 12168483 dated Nov. 9, 2012.

* cited by examiner

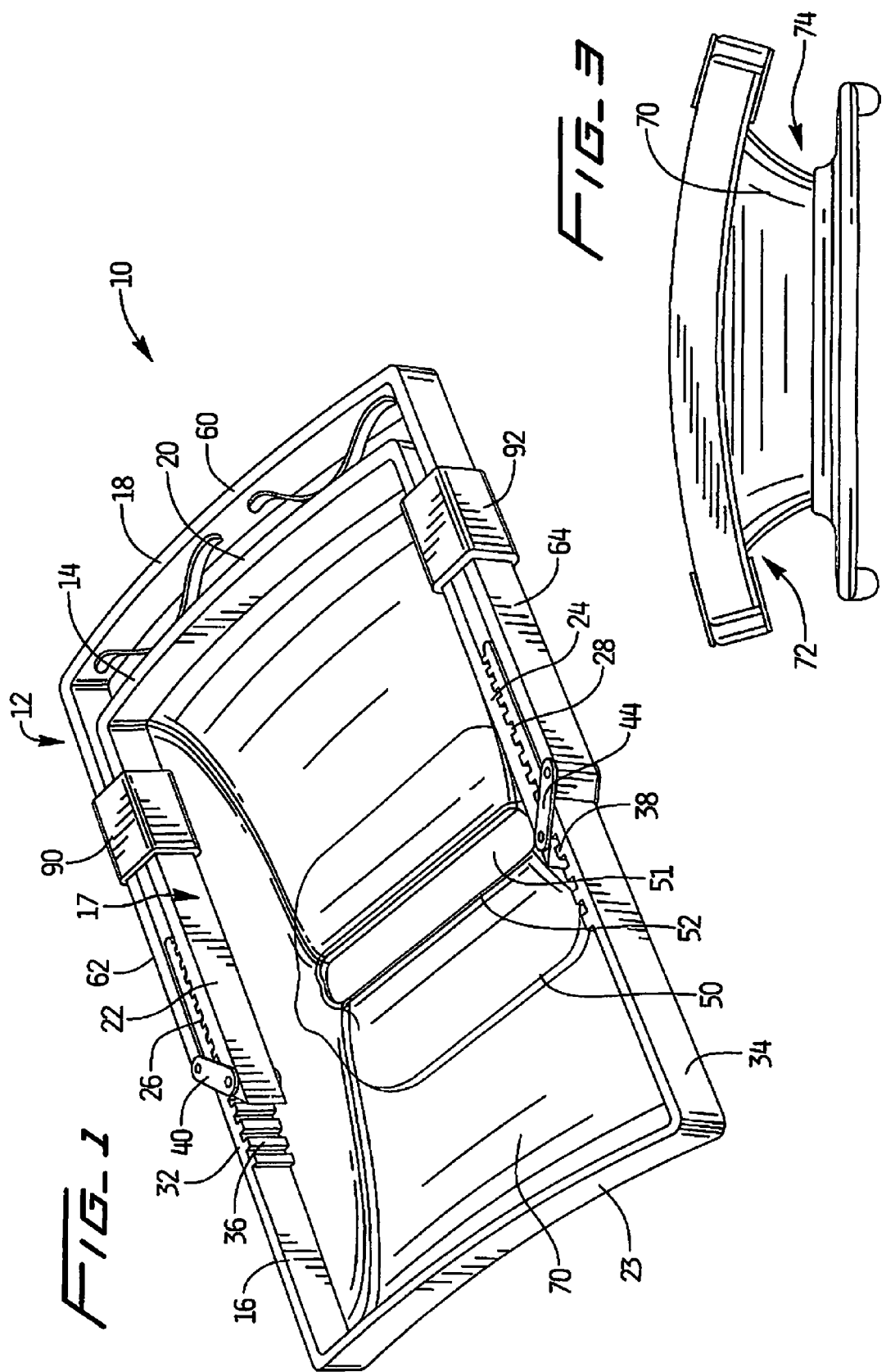

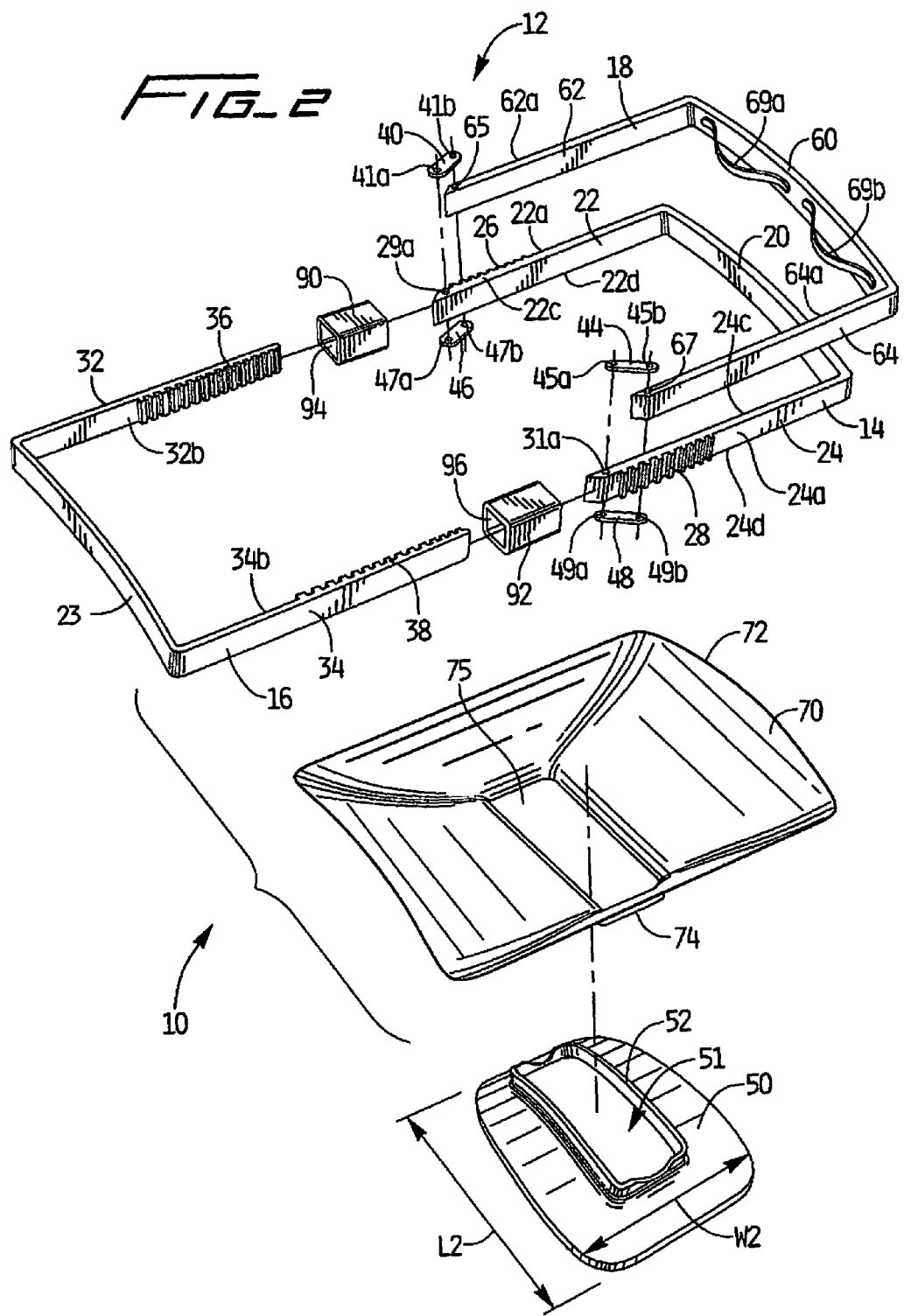

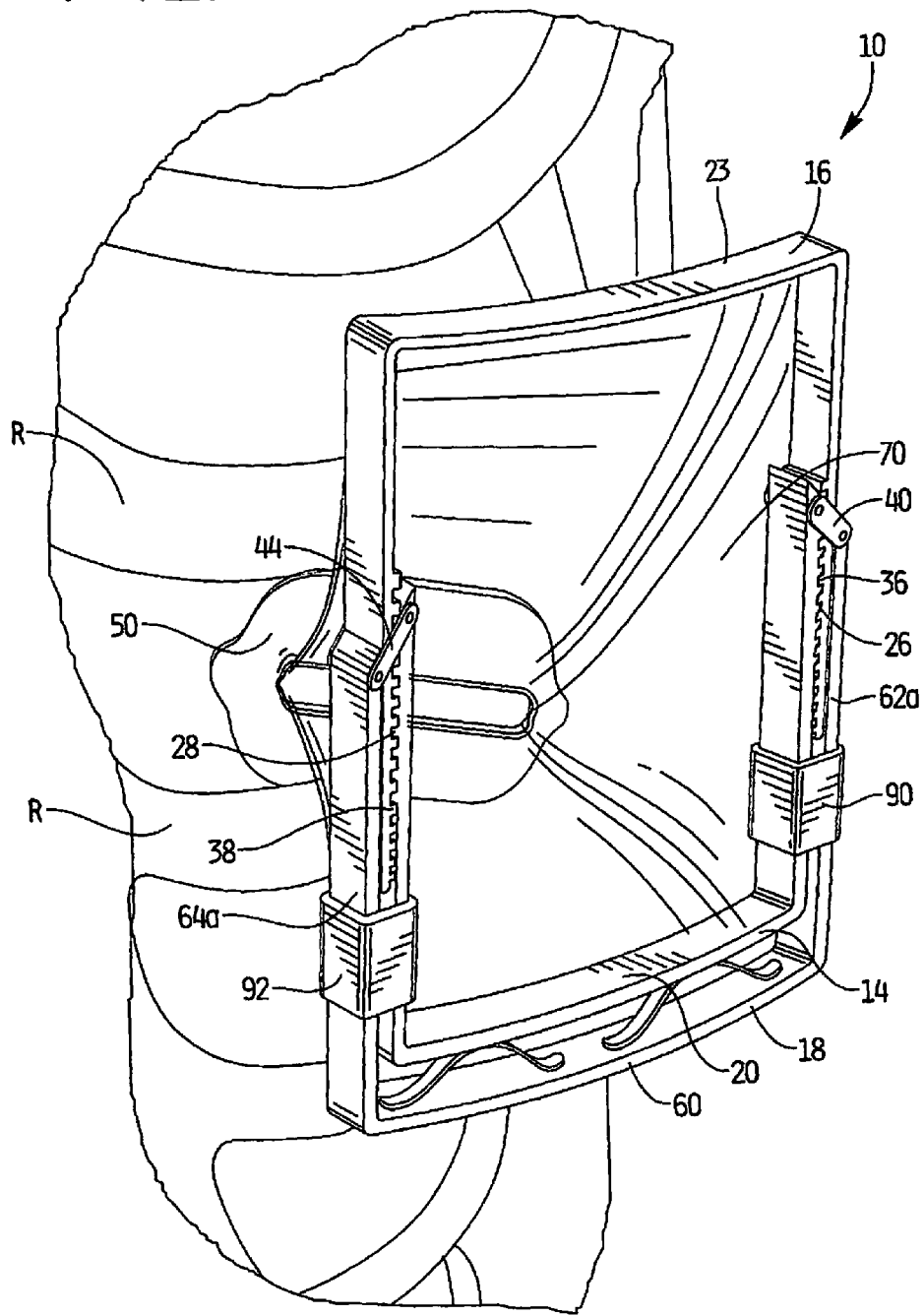

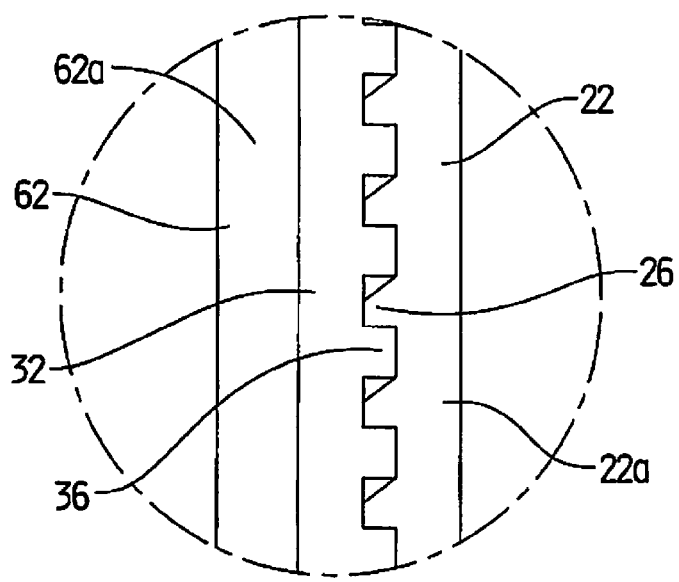
FIG_6
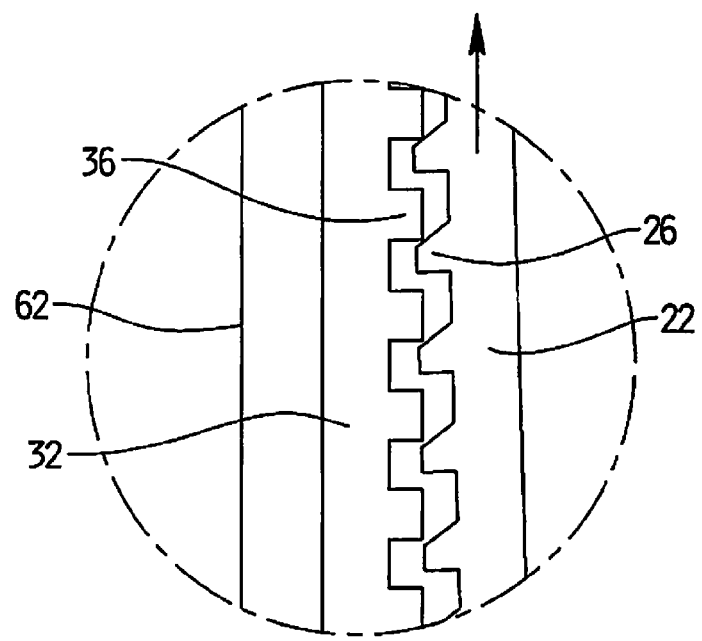
FIG_7

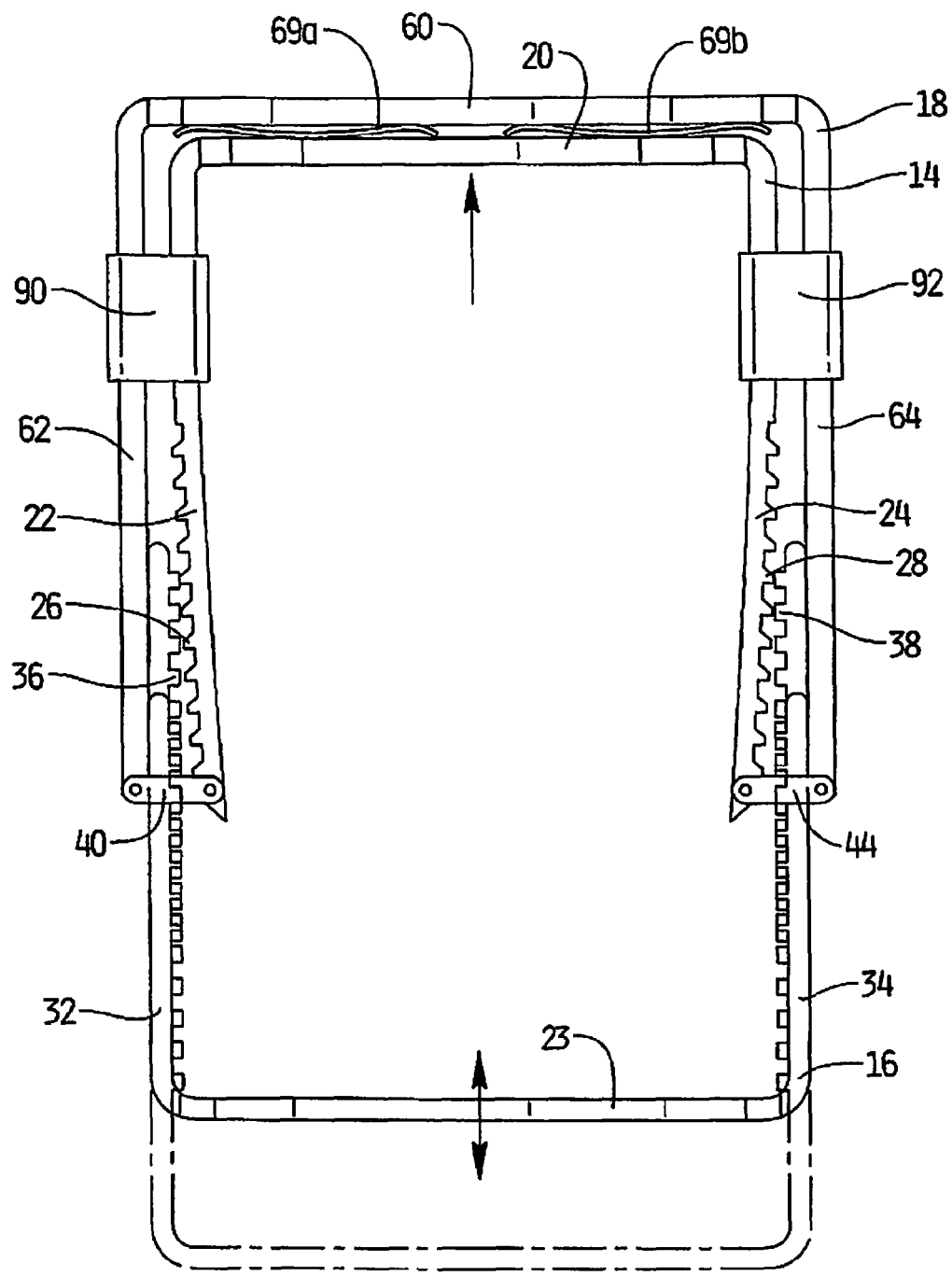
FIG_8

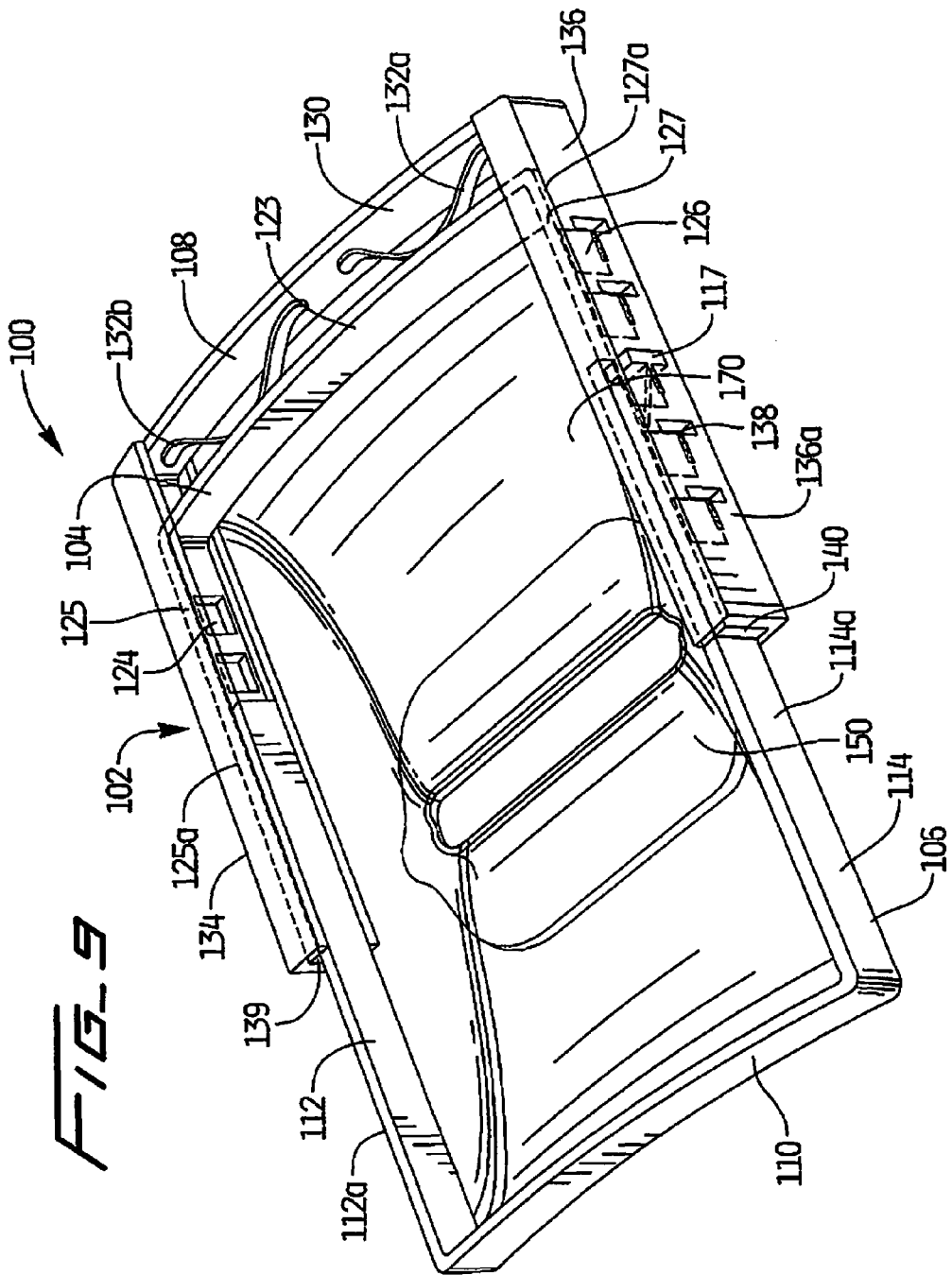

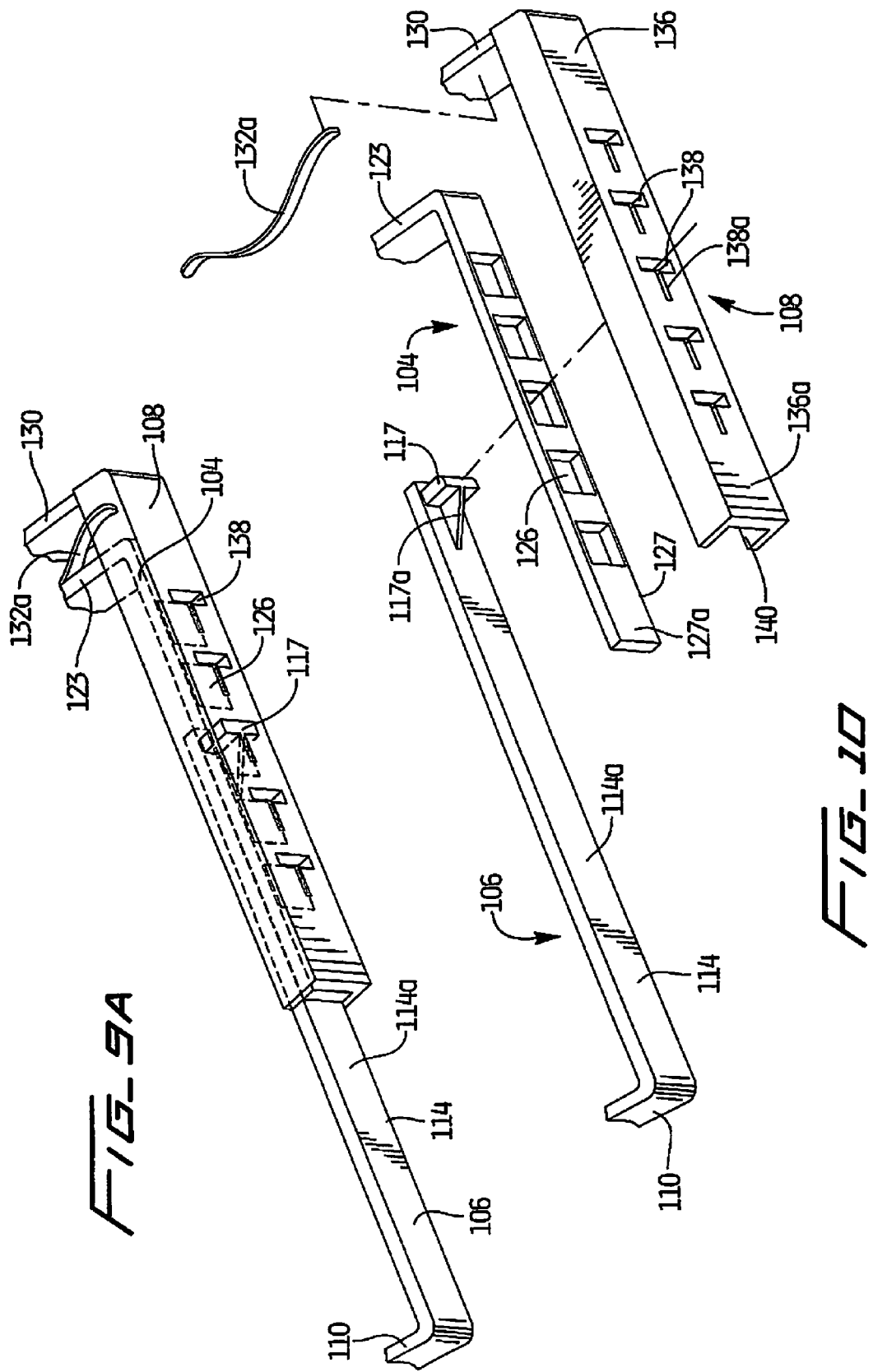

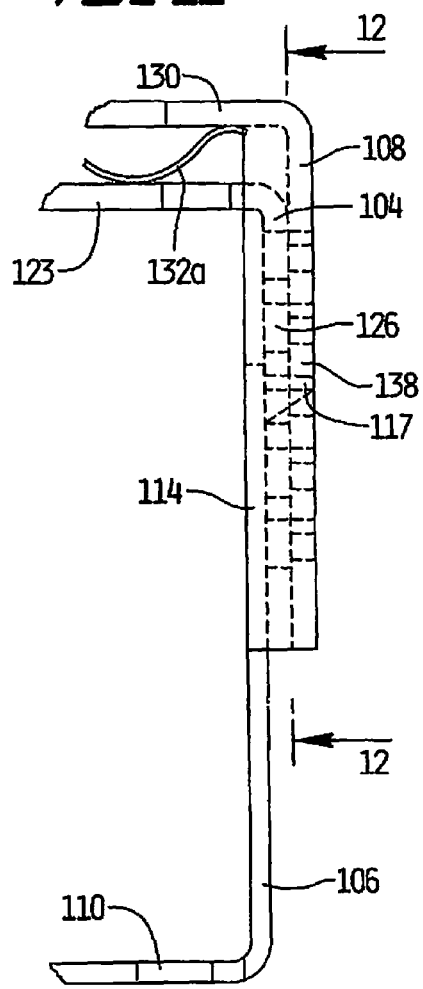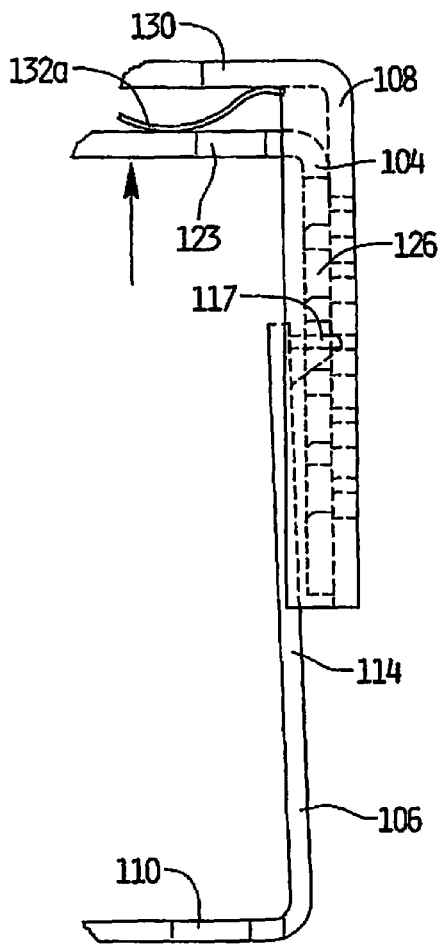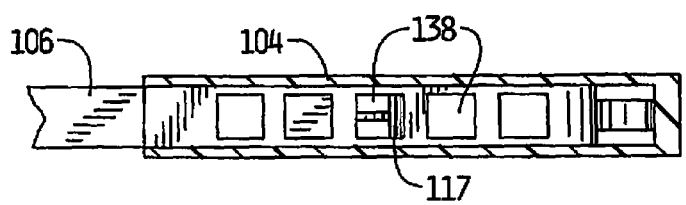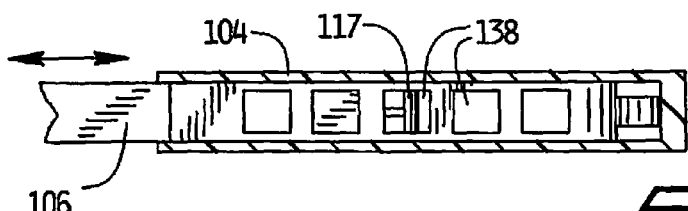

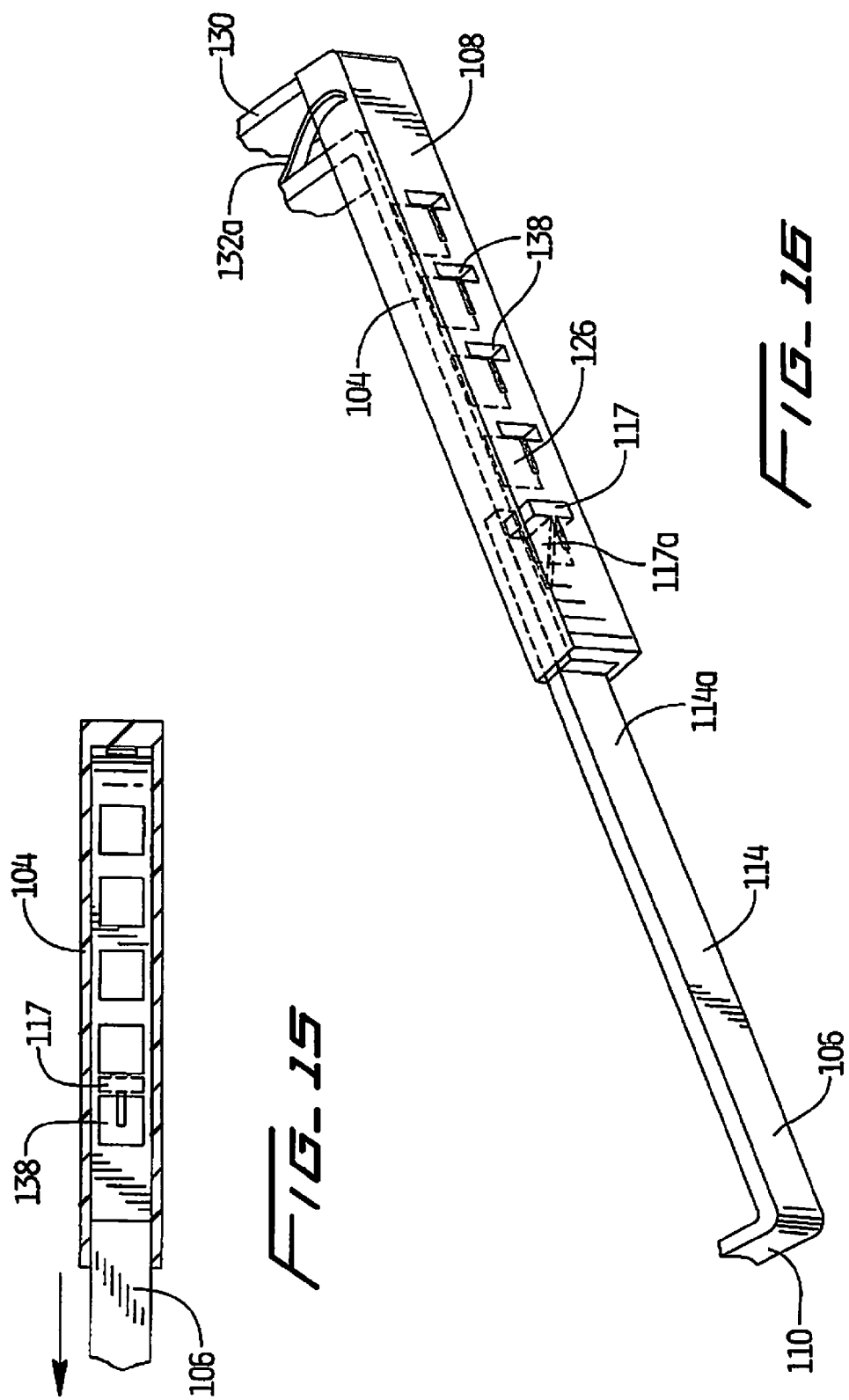

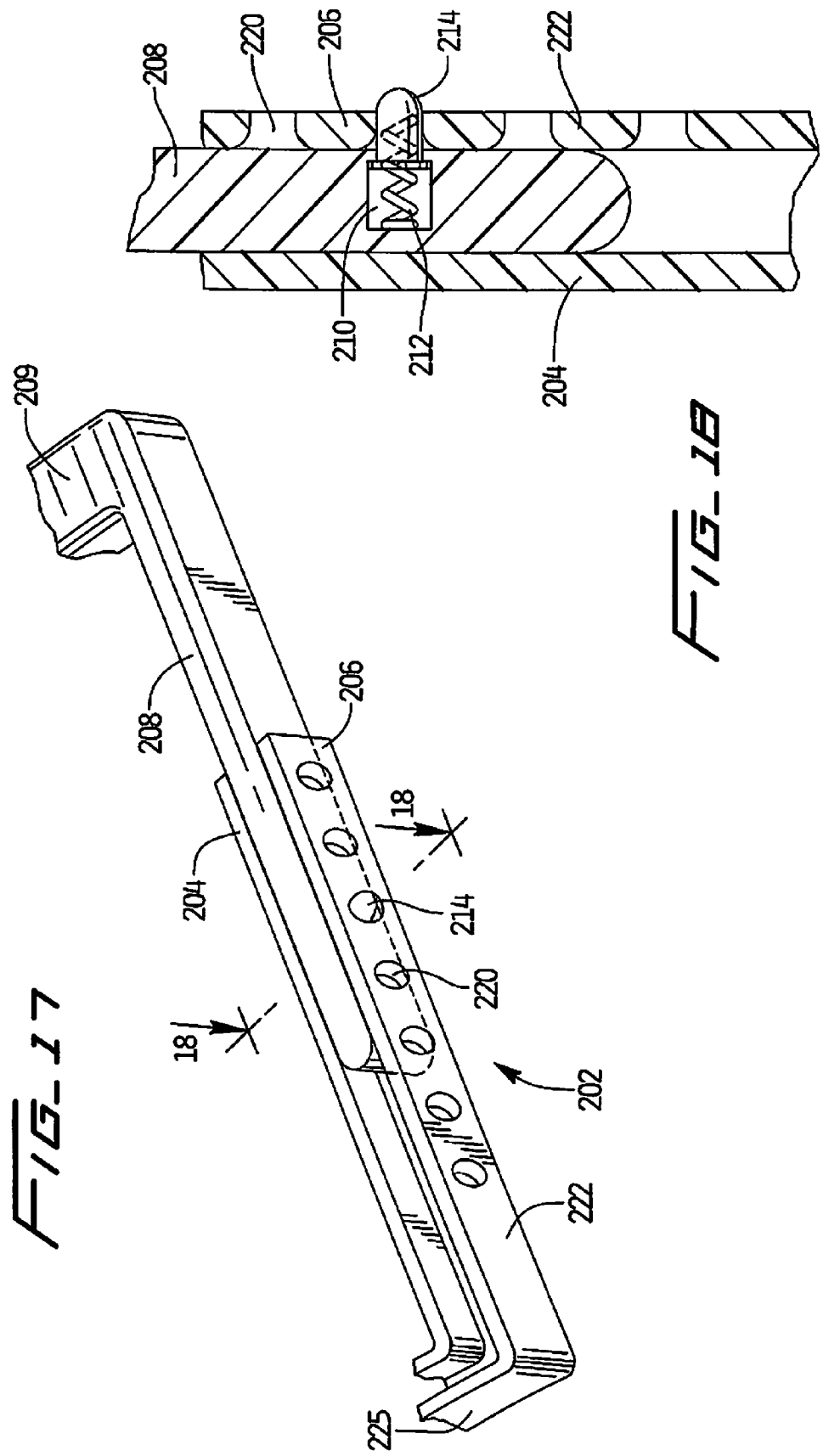

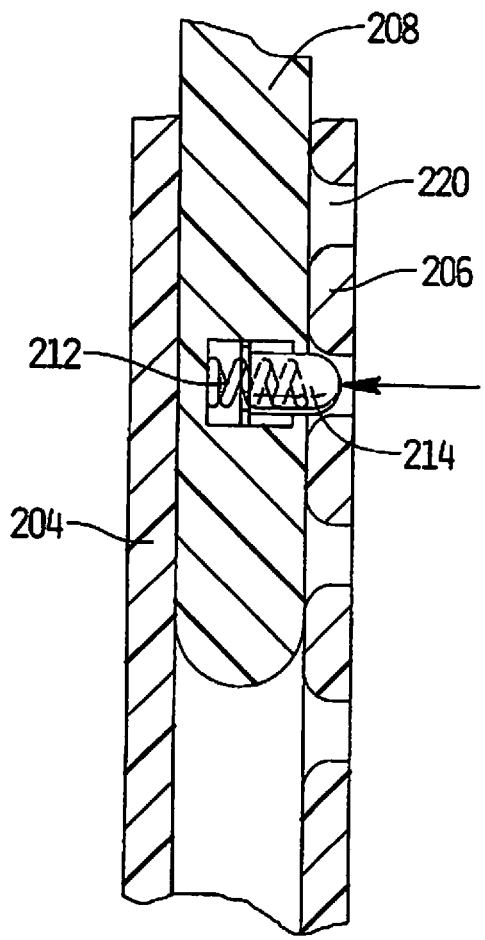
FIG_19
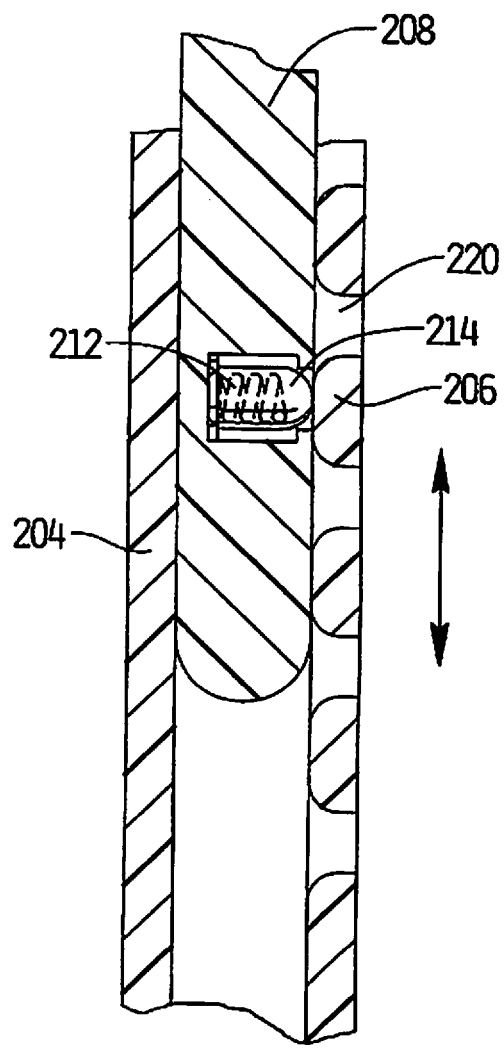
FIG_20

THORACIC ACCESS PORT

This application claims priority from provisional application Ser. No. 61/487,867, filed May 19, 2011, the entire contents of which are incorporated herein by reference.

BACKGROUND

1. Technical Field

The present disclosure relates generally to devices and techniques for performing surgical procedures. More particularly, the present disclosure relates to an expandable access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments can be inserted into the internal work site through the passageway in the access assembly.

In the interests of facilitating visualization, the introduction of certain surgical instruments, and/or the removal of tissue specimens during minimally invasive thoracic procedures, it may be desirable to spread the tissue adjacent the ribs defining the intercostal space. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for thoracic access ports which minimize post operative patient pain while enabling atraumatic retraction of tissue and which do not restrict access to the body cavity, as well as facilitate retrieval of tissue specimens from the body cavity and prevent tissue seeding or infection around the incision.

SUMMARY

In accordance with one aspect of the present disclosure, a surgical access assembly for positioning within an opening in tissue is provided. The surgical access assembly comprises an outer frame positionable outside a patient and defining an opening therein dimensioned to receive a surgical instrument therethrough. The outer frame has a first portion having a first engagement structure and a second portion having a second engagement structure, the first portion biased into locking engagement with the second portion such that the first engagement structure is in locking engagement with the second engagement structure. An inner member is positionable within a patient and a flexible member extends between the inner member and outer member and is operatively associated with the outer member. The first portion is movable to overcome the bias to move the first and second engagement structures to a disengaged position. In the disengaged position, at least one of the first and second portions is movable with respect to the other portion to adjust the tension on the flexible member to retract tissue.

In some embodiments, the access assembly includes a retaining frame having at least one spring to bias the first portion into locking engagement with the second portion. Preferably, the first portion is biased in an axial direction along a longitudinal axis of the outer frame.

In some embodiments the access assembly includes first and second links attached to the retaining frame and first portion, wherein movement of the first portion with respect to the retaining frame pivots the links to move the first engagement structure and the second engagement structure to the disengaged position.

In some embodiments, the first portion has an end wall and first and second arms extending therefrom and the second portion has an end wall and third and fourth arms extending therefrom, and pivoting of the links flexes the first and second arms radially inwardly from the third and fourth arms. The engagement structures can be positioned on the arms.

In some embodiments, the first engagement structure comprises a first set of teeth and the second engagement structure comprises a second set of teeth interlocking with the first set of teeth. In other embodiments, the second engagement structure comprises a locking tab and the first engagement structure comprises an opening dimensioned to receive the locking tab.

A retaining frame positioned external to the first and second portions can be provided. In some embodiments, an end wall of the first portion is movable toward an end wall of the retaining frame to move the first and second engagement structure to the disengaged position and subsequently movable away from the end wall of the retaining frame to return the first and second portions into locking engagement.

First and second pivotable link members can be provided connecting the retaining frame to the first portion. Movement of the first portion against the bias of a spring can pivot the links to a non-locking position to free the first and second portions for relative sliding movement.

In another aspect, the present disclosure provides a surgical access assembly for positioning within an opening in tissue, the surgical access assembly comprising an outer tensioning member having an opening dimensioned and configured to receive a surgical instrument therethrough. The outer member includes first and second portions, the first and second portions having a locking position with respect to each other and a release position. The first and second portions are spring biased to the locking position. The assembly further includes a flexible member extending distally with respect to the outer tensioning member, the flexible member being spread upon movement of at least one of the first and second portions away from the other portion to retract soft tissue adjacent the opening in tissue.

The assembly can further include in some embodiments a locking tab and an opening cooperating to interlock the first and second portions in the locking position. A retaining frame having a slot to receive the tab can be provided, wherein the first portion and retaining frame are relatively movable to move the first and second portions to the release position. A series of openings can be provided to selectively engage the tab to lock the first and second portions in one of several select spread positions. The locking tab can have an angled surface to facilitate movement out of the opening. In other embodiments, a plurality of interlocking teeth are positioned on the first and second portions to interlock the first and second portions in the locking position.

In some embodiments, a plurality of links are connected to the first portion, wherein pivoting of the links moves the first portion to the release position.

In another aspect, the present disclosure provides a surgical access assembly for positioning within an opening in tissue comprising an outer member positionable outside a patient and defining an opening therein dimensioned to receive a surgical instrument therethrough, and including first and second frame portions wherein at least one of the portions is movable, e.g., slidable, with respect to the other portion. An inner member is positionable within a patient and a flexible member extends between the inner member and outer member and is operatively associated with the outer member. A spring biased locking button cooperates with the second frame portion, and is movable to disengage from locking engagement with the second frame portion to enable relative movement of the first and second frame portions to tension the flexible member.

In some embodiments, the assembly further includes an intermediate frame positioned between the first and second frame portions, the intermediate frame having a recess to receive a spring to bias the locking button.

In another aspect, the present disclosure provides a method of accessing an internal cavity of a patient comprising the steps of:

forming an opening in a patient's tissue;
providing an access assembly including:
an outer member positionable outside a patient and defining an opening therein, the outer member including a first portion, a second portion, and a retaining member, at least one of the first and the second portion movable with respect to the other portion to adjust the opening, the opening dimensioned to receive a surgical instrument therethrough;
an inner member positionable within a patient; and
a flexible member extending between the inner member and outer member and operatively associated with the outer member, the flexible member having a passageway to receive a surgical instrument therethrough, wherein relative movement of the first portion and the second portion of the outer member adjusts the tension on the flexible member;
inserting the inner member through the opening in tissue within an intercostal space of the patient with the flexible member extending proximally through the opening in tissue;
moving at least one of the first portion and the retaining member toward the other to unlock the first and second portions; and
subsequently moving at least one of first and second portions away from the first portion to a select spread position to enlarge the opening in tissue; and
releasing the first portion to re-lock the first and second portions in the select spread position.

The method may further comprise the step of moving at least one of surgical instrumentation and tissue specimen through the passageway and opening in the tissue. The method may also include the step of folding the inner member for insertion within the intercostal space into the internal cavity.

BRIEF DESCRIPTION OF THE DRAWINGS

Various embodiments of the subject access port are described herein with reference to the drawings wherein:

FIG. 1 is a perspective view of one embodiment of the access port of the present disclosure;

FIG. 2 is an exploded perspective view of the access port of FIG. 1;

FIG. 3 is a side view of the access port of FIG. 1;

FIG. 4 is perspective front view illustrating a patient's skeletal structure with the surgical access port of FIG. 1 positioned within the intercostal space defined between adjacent ribs in accordance with the present disclosure, the access port shown in an initial (non-expanded) position;

FIG. 6 is an enlarged view of the area of detail of FIG. 5;

FIG. 7 is a view similar to FIG. 6 illustrating disengagement of the teeth for movement of the frames;

FIG. 8 is a top view similar to FIG. 5 illustrating release of the frames;

FIG. 9 is a perspective view of an alternate embodiment of the access port of the present disclosure;

FIG. 9A is a side perspective view of a portion of the frames of the access assembly of FIG. 9;

FIG. 10 is an exploded view of the portion of the frames of FIG. 9A;

FIG. 11 is a top view of a portion of the frames of FIG. 9 illustrating engagement of the frames;

FIG. 12 is a cross-sectional view taken along line 12-12 of FIG. 11;

FIG. 13 is a side view similar to FIG. 11 illustrating disengagement of the frames;

FIG. 14 is a view similar to FIG. 12 corresponding to the frame position of FIG. 13;

FIG. 15 is a view similar to FIG. 14 showing movement of the frame to a more spread position;

FIG. 16 is perspective view similar to FIG. 9A showing the frames in a more spread position;

FIG. 17 is a side perspective view of a portion of the frames of an alternate embodiment of the access assembly of the present disclosure;

FIG. 18 is a cross-sectional view taken along line 18-18 of FIG. 17;

FIG. 19 is a cross-sectional view similar to FIG. 18 showing pressing of the release button; and FIG. 20 is a cross-sectional view similar to FIG. 19 showing movement of the frames after depression of the release button.

DETAILED DESCRIPTION

Figure 5:
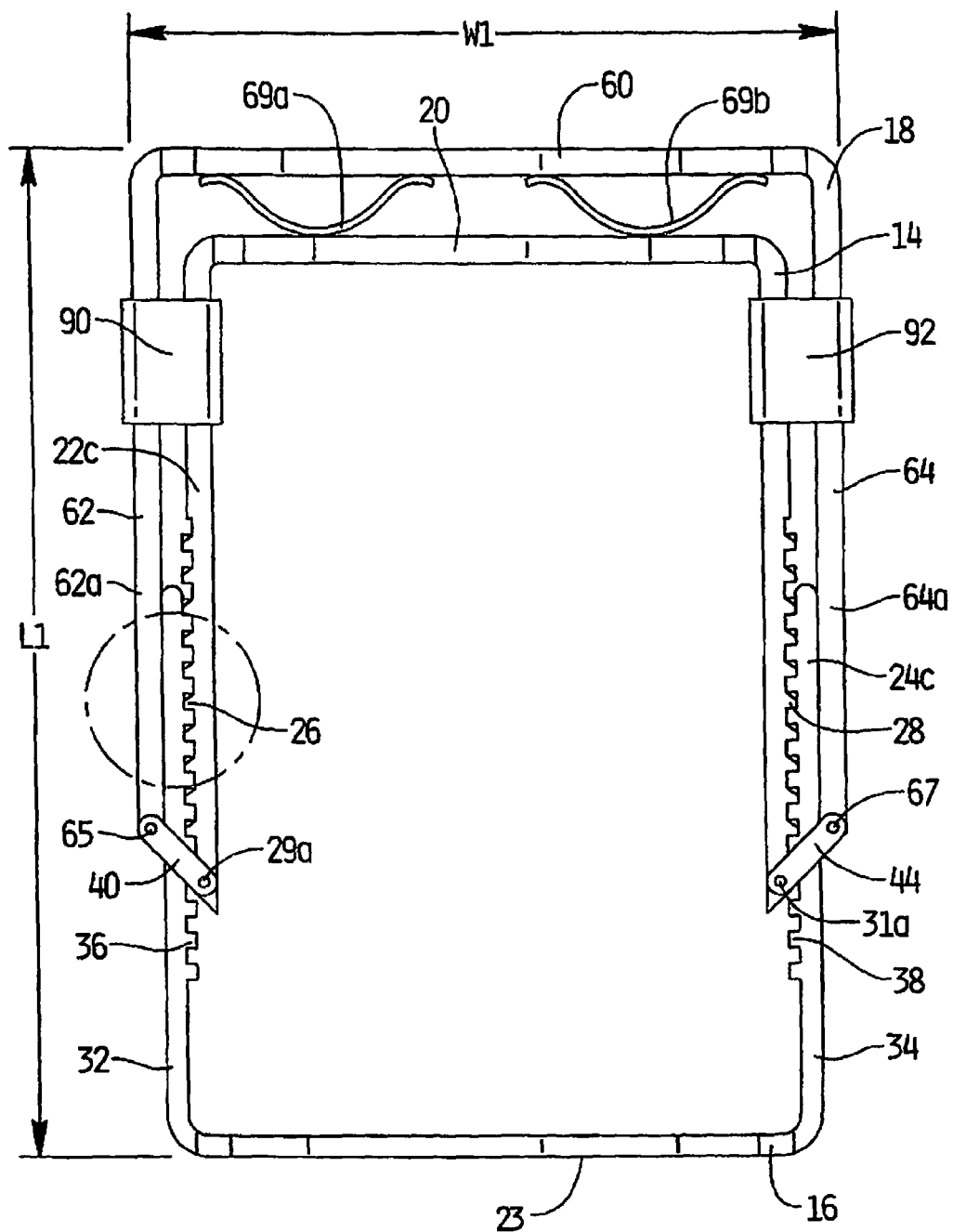
FIG. 5 is a top view of the access port of FIG. 1 in a first position.

Various embodiments of the presently disclosed access assembly, or access port, and methods of using the same, will now be described in detail with reference to the drawings wherein like references numerals identify similar or identical elements. In the drawings, and in the following description, the term "proximal" refers to the end of the access port, or component thereof, that is closer to the clinician and the term "distal" refers to the end that is further from the clinician, as is traditional and conventional in the art. It should be also be understood that the term "minimally invasive procedure" is intended to include surgical procedures through small openings/incisions performed within a confined space such as the thoracic cavity.

Referring now to FIGS. 1-8, a first embodiment of the presently disclosed surgical access port, generally identified by the reference numeral 10, is depicted as a thoracic port 10 that is configured and dimensioned for insertion into the intercostal space located between the adjacent ribs "R" (FIG. 4) of a patient in order to allow for the insertion and manipulation of one or more surgical instruments within the thoracic cavity. However, it is also envisioned that access port 10 may be configured and dimensioned to provide access to a variety of other internal body cavities and/or tissues. Access port 10 may be formed from any suitable biocompatible material of strength suitable for the purpose described herein, including, but not being limited to, polymeric materials.

The access port 10 is configured and dimensioned to extend into a body cavity, e.g., the thoracic cavity, through the intercostal space, and generally, with reference to FIGS. 1 and 2, includes an outer or proximal frame 12 having a first or inside frame or frame portion 14, a second or outside frame or frame portion 16 and a release/locking frame or frame portion 18. A flexible member, e.g. membrane 70, is coupled to outer frame 12 and extends distally therefrom. The distal end of the flexible member 70 is attached to distal or inner member 50. The outer frame 12 is movable between various spread positions to widen the passageway for insertion of instrumentation and to retract tissue. More specifically, portions 14 and 16 of frame 12 are relatively slidable to increase the distance between respective end walls 20, 22, and to increase the size of the opening 17 in the frame 12. The sliding of frame portions 14 and 16 applies tension to the flexible member 70 to retract tissue adjacent the incision in the patient to widen the access opening in the manner described below. It should be appreciated that although as described below the second portion 16 is slidable with respect to the first portion 14, it is also contemplated that the first portion 14 is slidable with respect to the second portion 16, or that both the first portion 14 and the second portion 16 are slidable. Thus, relatively slidable or slidable with respect to each other encompasses these alternatives.

As shown, the frame 10 is substantially rectangular in shape with a substantially rectangular opening. As can be appreciated, other shape frames and openings are also contemplated. Note also, that preferably the shape is elongated, e.g. has a length greater than its width.

It should be understood that the use of the term first and second portions and/or members or frames contemplates an assembly of several (separate) components or a unitary assembly.

Inner member 50 has an elongated opening 51 therethrough for passage of surgical instrumentation. The member 50 also has a nerve protecting wall or lip 52 extending along the opening 51, and preferably substantially surrounding the opening 51, and extending upwardly toward outer frame 12. The lip 52 facilitates attachment of the flexible membrane 70 thereto and can include proximally extending tabs (not shown) to facilitate such attachment. The member 50 is preferably composed of a substantially rigid material to provide anchoring of the access port while of sufficient flexibility to be bent or reconfigured for insertion as described below for fitting between the ribs of the intercostal space. The opening 51 is preferably non-circular in configuration, e.g. oval in configuration. Other configurations are also contemplated. In the illustrated embodiment, the inner frame 50 long dimension is positioned transverse to the direction of movement of the outer frame 112. Consequently, the longer dimension of the opening 51 is transverse to the longer dimension of the passageway 17 of the outer frame 12. Stated another way, the outer frame 12, at least in its expanded position, has a length L1 exceeding its width W1 (FIG. 5), the inner frame 50 has a length L2 exceeding its width W2 (FIG. 2), and the lengthwise dimension of the outer frame 12 is aligned with the widthwise dimension of the inner frame 50.

Flexible membrane 70 is generally funnel shaped, is coupled at its distal end 74 to lip 52 of inner member 50 and extends proximally therefrom. Proximal end 72 of flexible membrane 70 is coupled to an undersurface of end walls 20, 22 and isolates tissue surrounding access port 10 from the passageway extending therethrough, thus reducing the risk of tissue damage, seeding of cancerous cells, and/or infection during the surgical procedure. It can be attached by various methods such as welding, gluing or thermal bonding. It is envisioned that flexible membrane 70 is configured for soft tissue retraction. It is also envisioned that flexible membrane 70 be of sufficient elasticity to permit retraction of a wide range of tissue thicknesses since there may be a wide range of tissue thicknesses among different patients. It is also envisioned that flexible membrane 70 is of sufficient strength to prevent accidental tearing and/or puncture by surgical instrumentation inserted through access port 100. Additionally, it is envisioned that flexible membrane 70 be made from a biocompatible material to reduce the incidents of adverse reaction by a patient upon contact with the patient's tissue. Flexible membrane 70 may also be made of a transparent material to allow the surgeon to better visualize the surgical site and surrounding tissue. Flexible member 70 can be composed of polyurethane, although other materials such as silicone are also contemplated. It can be composed of a single member, a single member folded over and the edges attached forming a single seam, or alternatively two or more members attached together. For example, a two panel design with two seams or a four panel design with four seams, two on each side, can be utilized, with the flexible panels welded along the seam.

Outer frame 12 is preferably sufficiently rigid to retain membrane 70 in a tensioned configuration. As frame 12 is expanded (spread), membrane 70 is tensioned and stretched radially outwardly to retract tissue and/or to expand the passageway 75 extending through membrane 70.

Referring now to details of the outer frame 12, and with reference to FIGS. 1 and 2, first frame or frame portion 14 of outer frame 12 has arms 22 and 24 extending from end wall 20, preferably at substantially right angles thereto, although other angles are contemplated. Arm 22 has a series of teeth 26 along an outer side surface 22a thereof. Similarly, arm 24 has a series of teeth 28 extending along an outer side surface 24a. Thus, the teeth 26, 28 face away from a central longitudinal axis of the frame 12. The teeth 26, 28 are shown extending along a portion of the arms 22, 24, however, a shorter or longer longitudinal arrangement of the teeth along the sidewalls is contemplated.

Second frame or frame portion 16 of outer frame 12 has arms 32, 34 extending from end wall 23, preferably at substantially right angles thereto, although other angles are contemplated. Arm 32 has a series of teeth 36 along an inner surface 32b thereof. Similarly, arm 34 has a series of teeth 38 extending along an inner surface 34b, facing teeth 36. Thus, the teeth 36, 38 face toward the central longitudinal axis of the frame 12 (and toward teeth 26, 28, respectively). The teeth 36, 38 are shown extending along a portion of the arms 32, 34, however a shorter or longer longitudinal arrangement of the teeth along the sidewalls is contemplated. Teeth 28 and 38 and teeth 26 and 36 interlock as described below.

Upper surface 22c and lower surface 22d of arms 22, 24, respectively, of frame portion 14 each have a pin extending therefrom adjacent an end portion of the arm. More specifically, pin 29a extends upwardly or proximally from upper surface 22c to engage pivot hole 41a of link 40, and an opposing pin (not shown) extends downwardly or distally from lower surface 22d to engage pivot hole 47a of link 46. Similarly, upper surface 24c and lower surface 24d of arm 24 each have a pin extending therefreom adjacent an end portion of the arm. Pin 31a extends proximally from upper surface 24c and engages hole 45a of link 44 and an opposing pin (not shown) extends distally from bottom surface 24d to engage hole 49a of link 48. Links 40, 44, 46 and 48 also engage locking frame 18 described below.

Locking/release frame 18 has an end wall 60 and arms 62, 64 extending therefrom, preferably at substantially right angles thereto, although other angles are contemplated. Locking or retaining frame 18 is positioned external of frames 14, 16 such that arm 62 extends along or outside outer surface of arms 32 and 22 and arm 64 extends along or outside outer surface of arms 34 and 24 of respective frames 16 and 14 (arms 32 and 34 are external of arms 22, 24, respectively). Pin 65 extending from upper or proximal surface 62a of arm 62 is received in pivot hole 41b of link 40. An opposing pin on the lower surface of arm 62 extends distally and is received in pivot hole 47b of link 46. Pin 67 extending from upper or proximal surface 64a of arm 64 is received in pivot hole 45b of link 44. An opposing pin on the lower surface of arm 64 extends distally and is received in pivot hole 49b of pivot link 48.

Locking frame 18 has springs 69a, 69b extending from end wall 60 into contact with end wall 20 of frame portion 12 which bias frame 20 away from wall 60. In this biased position, the links 40, 44, 46 and 48 are at the angle shown in FIGS. 4 and 5. This maintains the frame portions 14, 16 in the normally engaged position due to the engagement of the respective teeth (26, 36 and 28, 38). In order to spread the frames 14, 16 apart (move end walls 20 and 22 away from each other), frame 60 and frame 14 are squeezed together, overcoming the bias of the springs 69a, 69b, thereby causing the links 40, 44, 46 and 48 to move to the more straightened position of FIG. 8 (e.g. substantially perpendicular to the longitudinal axis of the frame 12). This causes the arms 24, 26 of frame 14 to flex inwardly, thereby separating teeth 26 and 28 from teeth 36 and 38, respectively. In this flexed position, with the teeth disengaged, frames 14 and 16 can be moved away from each, i.e. increasing the distance between end walls 20, 23, thereby expanding the opening in the frame 12 and tensioning the membrane 70.

In this manner, the frame portions 14, 16 of the outer frame 12 can be moved apart to a desired spread position to expand and stretch the flexible membrane 70 and then the frame 14 is released, enabling it to return to a biased position and enabling the links 40, 44, 46, 48 to return to their original position so the arms 22, 24 return to their unflexed position of FIG. 4 so the frames 14, 16 are locked in the select spread position by the interlocking of the teeth in the new position.

Note that the collars 90 and 92 help hold the frames 18 and 14 together. In a preferred embodiment, the first and second collars 90, 92 are substantially identical and each has a respective opening 94, 96 (FIG. 2), therethrough for reception of the frames 18 and 14. The arms 62 and 22 of frames 18 and 14, respectively, are positioned through collar 90; the arms 64 and 24 of frames 18 and 14, respectively, are positioned through collar 92.

As can be appreciated, arms 22, 24 of frame 14 in their normal position are in engagement with arms 32, 34, respectively, of frame 16 such that the engagement structures in the form of interlocking teeth engage. In alternate embodiments, instead of teeth, engagement structures in the form of textured surfaces of high friction can be utilized such as beads, ridges, domes and/or points which interlock with a textured surface of the other frame. Alternatively, a plurality of projections, e.g. domes or balls, can be provided to provide for engagement of the frame portions 14, 16 to help retain them in position.

The use of the access port 10 of FIGS. 1-8 will now be described in conjunction with the embodiment of FIG. 1, it being understood that the embodiment of FIG. 9 discussed below would work in a similar fashion, the difference being the differing engagement structures of the inner and outer surfaces of the frames.

The use of the access port 10 is described for thoracic surgery, it being understood that it and the other access ports disclosed herein can be utilized in other procedures.

Initially, an opening, or incision, is made in the patient's outer tissue wall of the thoracic body cavity by conventional means. The incision is made between adjacent ribs "R" (FIG. 4), extending along the intercostal space, and is relatively narrow and elongated.

For insertion through the incision, the inner member 50 is bent or reconfigured to reduce its transverse dimension for insertion through the patient's incision and into the body cavity. Note different sizes of access ports can also be used to accommodate different patients.

With access port 10 in the position of FIG. 4, the inner frame 50 is positioned within the body cavity adjacent the inner portion of the incision, with flexible membrane 70 extending through the incision to outside the patient's body and outer (upper) frame 12 (portions 14, 16) resting on the patient's skin. The outer frame 12 can now be expanded. Note the longitudinal axis of the inner frame 50 is substantially parallel to a long axis of the incision and the longitudinal axis of outer frame 12 is substantially transverse to a long axis of the incision, the longitudinal axis defined along the length of the respective frame which exceeds its width.

In the initial position of access port 10, flexible membrane 70 defines a funnel shape with frame 12 (portions 14, 16) retaining proximal end 72 of flexible membrane 70 while distal end 74 of flexible membrane 70 defines a smaller diameter due to the engagement of distal end 74 with the smaller inner frame 50. That is, since the width and length of outer frame 12 are greater than the width and length of the lip 52 of the inner member 50 to which the membrane 70 is attached at its distal end, a funnel shape is formed. In this initial position, lip 52 is configured to seat a rib "R" of a patient therein to protect the rib "R," the intercostal nerve, and surrounding tissue. That is, lip 52 extends upwardly (proximally) into the opening in tissue adjacent the ribs "R," i.e., within the thoracic cavity. Additional cushioning (not shown) may be provided to provide further protection to the ribs and to surrounding tissue. Outward flexion of flexible membrane 70 due to expansion of the outer frame 12 expands the intercostal space, e.g. by spreading tissue adjacent the ribs, thus maximizing the passageway to the cavity, and giving access port 10 the maximum length. In the initial position, the respective teeth of frames 14 and 16 are engaged as shown in FIGS. 4, 5 and 6.

To spread the first and second sections 14, 16 of frame 12 to stretch (radially tension) the flexible membrane 70 to retract tissue adjacent the ribs and incision and widen the incision passageway for instrumentation insertion, the end wall 20 of the second frame 14 and the end wall 60 of the locking frame 18 are pressed toward each other by the user, thereby reducing the distance between end walls 20 and 60 as end wall 20 moves toward end wall 60 (see FIG. 8). This causes the arms 22, 24 of frame 14 to flex inwardly due to the pivoting of the links 40, 44, 46, 48 from the angled position of FIGS. 4 and 5 to the more straightened positioned of FIG. 8. Such flexing causes the arms 22, 24 and their engagement structure, e.g. teeth 26, 28, to flex inwardly toward a longitudinal axis of the frame 12 and away from respective arms 32, 34 to disengage from teeth 36, 38, respectively, of frame 16 (see FIGS. 7 and 8). This disengagement enables the user to grasp the frame 16, e.g. by grasping end wall 23 or arms 32 and 34, and moving it away from frame 14. This relative sliding movement tensions flexible membrane 70. The movement and more spread position of frame 16 are shown in phantom in FIG. 8. Note the tissue is spread transverse to the long axis of the incision.

When the desired spread position, i.e. desired tissue retraction, is achieved, the surgeon releases the grasp of frame 14 and locking frame 18, allowing frame 14 to return to its normal position under the bias of springs 69a, 69b, as the links 40, 44, 46, 48 return to the their angled position of FIGS. 4 and 5, with engagement surfaces moved from a non-engaged position to an engaged position to lock (secure) the first and second frames 14, 16 in the select position. This engagement of the engagement structures (e.g. teeth 26, 36 and 28, 38) enhances the securement of the two frames 14, 16 by limiting slippage as the bias of locking/release frame 18 locks the frames against movement.

With access port 10 secured in the desired expanded position, surgical instrumentation may be inserted through passageway 17 (in outer frame 12), passageway 75 (in flexible member 70) and opening 51 in inner frame 50 to perform the surgical procedure within the body cavity. The low-profile configuration of access port 10, along the external surface of tissue, allows for greater access to the thoracic cavity and for greater manipulation of instrumentation disposed through the passageway.

Upon completion of the surgical procedure, frame 14 and release frame 18 can once again be moved toward each other, to release the arms 22, 24, to allow them to move to their unlocked non-engaged position, thereby allowing the frame portions 14, 16 to be moved toward each other to untension flexible membrane 70. Next, the surgeon may grasp inner member 50 to fold or reconfigure it to reduce its transverse dimension to remove it from the body cavity and through the incision.

As will be appreciated, access port 10 is easily inserted, manipulated, and removed from a patient's body. Further, the access port 10 is minimally intrusive, flexible to conform to a patient's anatomy, and provides good visibility into the thoracic cavity. Additionally, the low-profile configuration of access port 10 is particularly advantageous, for example, in the removal, or retrieval, of tissue specimens from within the body.

FIGS. 9-16 illustrate an alternate embodiment of the access port of the present disclosure, designated by reference numeral 100. The access port 100 of FIG. 9 is similar to access port 10 of FIG. 1 in that it has an inner (distal) frame 150 and a flexible member (e.g. membrane) 170 identical to that of FIG. 1 having openings to access the body cavity. Thus, details of frame 150 and member 170 are not repeated herein. The difference between the two ports 100 and 10 is the outer (proximal) frame which functions to tension and retain the flexible member 170.

Outer frame 102 of access port 100 has a first frame or frame portion 104, a second frame or frame portion 106 and a locking release frame or frame portion 108. First and second frames 104, 106 are relatively slidable to tension membrane 170 as described below.

Second frame 106 has an end wall 110 with side arms 112, 114, extending therefrom, preferably at substantially right angles thereto, although other angles are contemplated. A locking (engagement) tab 117 extends from a side surface 114a of arm 114, extending radially outwardly away from a longitudinal axis of the outer frame 102. A similar locking (engagement) tab extends from side surface 112a of arm 112, extending radially outwardly away from a longitudinal axis of frame 102. Engagement tab 117 includes an angled portion 117a, best shown in FIG. 10, to facilitate disengagement from a selected opening in the frames 104, 108 discussed below.

First frame 104 includes a plurality of openings 124, 126 extending through a respective side wall 125a, 127a on each arm 125, 127. Openings 124, 126 are each configured and dimensioned to receive a locking tab of second frame 106. Arms 125, 127 extend from end wall 123, preferably at substantially right angles thereto, although other angles are contemplated.

Locking or retaining frame 108 includes an end wall 130 and has springs 132a, 132b to bias frame 104 away from end wall 130. Arms 134, 136 extend from end wall 130, preferably at substantially right angles thereto, although other angles are contemplated. Locking frame 108 further includes a series of slots 138 formed in side wall 136a of arm 136. A similar series of slots is formed in the side wall of arm 134. The slots on each side wall are configured and dimensioned to receive the locking tabs of frame 106. Note the slots 138 have a transverse slot portion 138a to accommodate angled portion 117a of tab 117. The arms 134, 136 of locking frame 108 each have a channel 139, 140, respectively, to slidingly receive the arms of the frames 104, 106. Note that locking frame 108 forms the outermost frame portion and first frame 104 is positioned between locking frame 108 and second frame 106, best shown in FIGS. 9 and 9A.

First frame 104 is biased in a direction away from wall 130 of locking frame 108 by springs 132a, 132b. In this initial position (see FIGS. 9, 11 and 12), a first engagement tab 117 of frame 106 extends through a select opening 126 in arm 127 of frame 104 and a select slot 138 in arm 136 of locking frame 108. A second identical engagement locking tab on the opposing side of frame 106 (on arm 112) extends through a select opening 124 in arm 125 of frame 104 and a select slot in arm 134 of locking frame 108. This maintains the frames 104, 106 in a locked/retained position.

In use, to release the frames 104, 106 to enable spreading of the frames and tensioning of the membrane 170 to retract tissue adjacent the incision, end walls 130 and 123 of frames 104, 108, respectively, are pressed together by the user, overcoming the bias of the springs 132a, 132b. This forces engagement tabs 117 on arms 112, 114 of frame 106 out of the slots in locking frame 108 as the two tabs 117 are cammed out of the slots, aided by the angled surface 117a of tab 117 (FIG. 13). This enables the first and second frames 104, 106 to be moved (slid) apart as shown in by the arrow in FIG. 13 as the tabs exit openings 124, 126. Such sliding movement of the frames 104, 106 tensions the membrane 170. Note that frame 106 can be moved relative to frames 104, 106, frame 104 can be moved relative to frame 106, or both frames can be moved relative to each other. Thus, sliding movement or relative movement of the frames contemplates each of these.

When the desired select spread position of the frame portions 104, 106 is achieved, and tabs 117 are moved into the desired openings 124, 126 of frame 104, the locking frame 108 and first frame 104 can be released, allowing frame 104 to move under the bias of springs 132a, 132b, away from wall 130 of locking frame 108, thereby leaving the tabs 117 in locking engagement as they each extend through a select slot in arms 134, 136 of locking frame 108. (Compare FIGS. 11 and 12 with FIGS. 15 and 16). In this new locked position, frames 104, 106 are locked against sliding movement to retain the membrane 170 in the tensioned position. Surgical instrumentation can then be inserted through the passageway in access port 100 formed through outer frame 102, membrane 170 and inner frame 150 to access the cavity, e.g. the thoracic cavity. FIGS. 15 and 16 illustrate the tab 117 engaging the opening 126 of frame 104 and slot 138 of frame 108 corresponding to the most spread position of the frames 104, 106 as the tab 117 is engaged in the last of the openings and slots of frames 104, 108. The tab on the opposing side of frame 106 would likewise be locked in the corresponding last opening and slot of frames 104, 108. As can be appreciated, if less tensioning of the membrane 170 is desired, the tabs 117 can be locked within another opening and slot of the frames 104, 108. Note a different number of openings and slots than the number illustrated is also contemplated.

To remove the access port 100 at the end of the surgical procedure, locking frame 108 and frame 104 are again pressed together by the user pressing walls 123, 130 toward each other. This forces locking tabs 117 out of engagement with the slots 138 as the arms 114, 112 of frame 106 flex inwardly as in the flexing of FIG. 13, freeing frames 106, 104 for relative movement. The frames 104, 106 can then be moved toward each other to reduce the tension on the membrane 170. Inner frame 150 is then removed from the body cavity.

FIGS. 17-20 illustrate another alternate embodiment of the present disclosure. In this embodiment a release/locking button is utilized to unlock the frames to allow sliding movement to spread the frames and tension the membrane. The embodiment of FIGS. 17-20 can be used with the flexible member 70 and inner frame 50 of FIG. 1 and therefore the components are not shown in these Figures or further described herein.

Outer frame 202 in this embodiment includes a first frame 204, a second frame 206 and a third locking frame 208 having a release button extending therefrom. Locking frame 208 is interposed between frames 204 and 206. Only portions of the frames are shown, it being understood that the frames are shaped similar to frames 104, 106 and 108 of access port 100.

More specifically, first frame or frame portion 204 is fixedly attached to locking frame 208. Locking frame 208 includes a cutout 210 to receive a spring 212 to bias a release button 214 into a locking position, radially outwardly from frame 208. Second frame or frame portion 206 has a plurality of longitudinally spaced openings 220 formed in a sidewall 222 configured and dimensioned to receive locking button 214. An identical locking button is formed on the opposing side of frame 208, seated in a cutout and biased outwardly by a spring as in button 214, to engage openings identical to openings 220 on the opposing side of frame 206.

In the initial position, locking button 214 is spring biased outwardly to extend through one of the openings 220 on each side of second frame 206. After insertion of the inner member, e.g. member 50, inside the body cavity, to tension the flexible membrane, the user presses in the buttons 214 on each side of the frame and then moves the locking frame 208 and/or second frame 206 away from each other. Note movement of the locking frame 208 carries the first frame 204 which is secured thereto. When the release button 222 on each side becomes aligned with the next opening 220 in frame 206, it moves into the opening 220 under the bias of the spring 212 to lock the frames 208, 206 in the select spread position. If further spreading of the frames to further tension the membrane is desired, the buttons 214 once again can be pressed in and the frames slid further apart, thus providing the incremental spreading of the frames and tensioning of the membrane.

At the end of the procedure, to untension the membrane, locking button 214 is pressed inwardly to release frame 206 for relative sliding movement of locking frame 208 and second frame 206 toward each other, i.e., move end wall 209 of locking frame 208 and end wall 225 of frame 206 toward each other.

Note the flexible membranes described herein may be coated with a lubricant, or gel, to aid in the insertion and removal of surgical instrumentation and/or tissue specimens from the access port.

Although described for use in thoracic procedures, it should also be understood that the access ports described herein can be used in other minimally invasive surgical procedures.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A surgical access assembly for positioning within an opening in tissue, the surgical access assembly comprising:
   an outer frame positionable outside a patient and defining an opening therein, the opening dimensioned to receive a surgical instrument therethrough, the outer frame including first and second portions, the first portion having a first engagement structure and the second portion having a second engagement structure;
   an inner member positionable within a patient;
   a flexible member extending between the inner member and the outer frame and operatively associated with the outer frame;
   a retaining frame having at least one spring to bias the first portion into locking engagement with the second portion such that the first engagement structure is in locking engagement with the second engagement structure, the first portion being biased in a first axial direction along a longitudinal axis of the outer frame; and
   first and second links, each of the first and second links attached to the retaining frame and the first portion,
   wherein movement of the first portion with respect to the retaining frame in a second, opposite axial direction along the longitudinal axis overcomes the bias and pivots the first and second links to move the first and second engagement structures to a disengaged position, and wherein, in the disengaged position, at least one of the first and second portions is movable with respect to the other portion to adjust the tension on the flexible member to retract tissue.

2. The access assembly of claim 1, wherein the first portion has an end wall and first and second arms extending therefrom and the second portion has an end wall and third and fourth arms extending therefrom, and pivoting the first and second links flexes the first and second arms radially inward from the third and fourth arms.

3. The access assembly according to claim 1, wherein the first engagement structure comprises a first set of teeth and the second engagement structure comprises a second set of teeth interlocking with the first set of teeth.

4. The access assembly of claim 3, wherein the first set of teeth is on an outer surface of the first portion and the second set of teeth is on an inner surface of the second portion.

5. The access assembly according to claim 1, wherein the retaining frame is positioned external to the first and second portions.

6. The access assembly according to claim 1, wherein the second engagement structure comprises a locking tab and the first engagement structure comprises an opening dimensioned to receive the locking tab.

7. The access assembly according to claim 1, wherein an end wall of the first portion is movable toward an end wall of the retaining frame to move the first and second engagement structures to the disengaged position and subsequently movable away from the end wall of the retaining frame to return the first and second portions into locking engagement.

8. A surgical access assembly for positioning within an opening in tissue, the surgical access assembly comprising:
   an outer tensioning member defining a longitudinal axis and having an opening dimensioned and configured to receive a surgical instrument therethrough, the outer tensioning member including first and second portions, the first and second portions having a locking position with respect to each other and a release position;
   a retaining frame having at least one spring to bias the first portion in a first axial direction along the longitudinal axis towards the locking position;
   first and second pivotable link members coupled between the retaining frame and the first portion, wherein movement of the first portion in a second, opposite axial direction along the longitudinal axis with respect to the retaining frame overcomes the bias and pivots the first and second link members to move the first portion to the release position; and
   a flexible member extending distally with respect to the outer tensioning member, wherein, in the release position of the first and second portions, the flexible member is spread upon movement of at least one of the first and second portions away from the other portion to retract soft tissue adjacent the opening in tissue.

9. The access assembly according to claim 8, further comprising a locking tab and an opening cooperating to interlock the first and second portions in the locking position.

10. The access assembly of claim 8, further comprising a plurality of interlocking teeth on the first and second portions to interlock the first and second portions in the locking position.

* * * * *